US009522755B2

(12) United States Patent
Scheuren et al.

(10) Patent No.: US 9,522,755 B2
(45) Date of Patent: Dec. 20, 2016

(54) APPARATUS AND METHOD FOR STERILIZING CONTAINERS

(71) Applicant: KRONES AG, Neutraubling (DE)

(72) Inventors: Hans Scheuren, Bad Kreuznach (DE); Josef Knott, Schierling (DE); Katharina Seidenberg, Karlsruhe (DE); Michael Neubauer, Uebersee (DE)

(73) Assignee: Krones, AG, Neutraubling (DE)

( * ) Notice: Subject to any disclaimer, the term of this patent is extended or adjusted under 35 U.S.C. 154(b) by 13 days.

(21) Appl. No.: 14/460,539

(22) Filed: Aug. 15, 2014

(65) Prior Publication Data
US 2015/0071818 A1 Mar. 12, 2015

(30) Foreign Application Priority Data

Sep. 6, 2013 (DE) .................. 10 2013 109 794

(51) Int. Cl.
*B65B 55/16* (2006.01)
*A61L 2/08* (2006.01)
(Continued)

(52) U.S. Cl.
CPC ................ *B65B 55/16* (2013.01); *A61L 2/087* (2013.01); *B29C 49/42* (2013.01); *B65B 55/08* (2013.01); *H01J 29/06* (2013.01); *A61L 2202/23* (2013.01)

(58) Field of Classification Search
CPC .......... B65B 55/16; B65B 55/08; A61L 2/087; B29C 49/42; H01J 29/06
See application file for complete search history.

(56) References Cited

U.S. PATENT DOCUMENTS 6,221,216 B1 * 4/2001 Nablo ................ A61L 2/08
204/157.15
7,145,155 B2 * 12/2006 Nablo ................ A61L 2/08
250/492.1
(Continued)

FOREIGN PATENT DOCUMENTS

DE 2011055553 5/2013
EP 2769922 8/2014
(Continued)

OTHER PUBLICATIONS

Extended European Search Report dated Feb. 5, 2015 issued in corresponding European Application No. 14183893.8-1356.
(Continued)

Primary Examiner — Regina M Yoo
(74) Attorney, Agent, or Firm — Onello & Mello, LLP.

(57) ABSTRACT

An apparatus for sterilizing containers, comprises a transport device which transports the containers along a predefined transport path and at least one sterilization device which bombards the containers with charge carriers for sterilization during a transport of the containers along the transport path. The at least one sterilization device comprises a generating device for generating charge carriers. The apparatus further comprises a screening device for screening radiation. The screening device surrounds the transport path of the containers at least in portions. The screening device comprises: a first wall adjacent the transport path of the containers; and a second wall below the transport path of the containers, wherein the second wall is movable relative to the transport path of the containers.

17 Claims, 2 Drawing Sheets

(51) Int. Cl.
    B29C 49/42    (2006.01)
    B65B 55/08    (2006.01)
    H01J 29/06    (2006.01)

(56) References Cited

U.S. PATENT DOCUMENTS

| | | |
|---|---|---|
| 8,636,949 B2 | 1/2014 | Bufano et al. |
| 8,729,499 B2 | 5/2014 | Knott et al. |
| 2011/0016829 A1 | 1/2011 | Drenguis et al. |
| 2012/0134878 A1 | 5/2012 | Silvestri |
| 2012/0145929 A1 | 6/2012 | Nishino et al. |
| 2012/0273694 A1 | 11/2012 | Lejeune et al. |
| 2013/0129566 A1 | 5/2013 | Knott et al. |
| 2013/0221244 A1* | 8/2013 | Shibuya .................. H01J 33/04 250/492.3 |
| 2014/0299786 A1 | 10/2014 | Yokobayashi et al. |
| 2014/0369885 A1 | 12/2014 | Krueger |

FOREIGN PATENT DOCUMENTS

| | | |
|---|---|---|
| JP | 2003121597 | 4/2003 |
| JP | 200856282 | 3/2008 |
| WO | 2009095182 | 8/2009 |
| WO | 2010128532 | 11/2010 |
| WO | 2013058205 | 4/2013 |
| WO | 2013092735 | 6/2013 |

OTHER PUBLICATIONS

German Search Report dated Jun. 11, 2014 in corresponding German Application No. 10 2013 109 794.4.

* cited by examiner

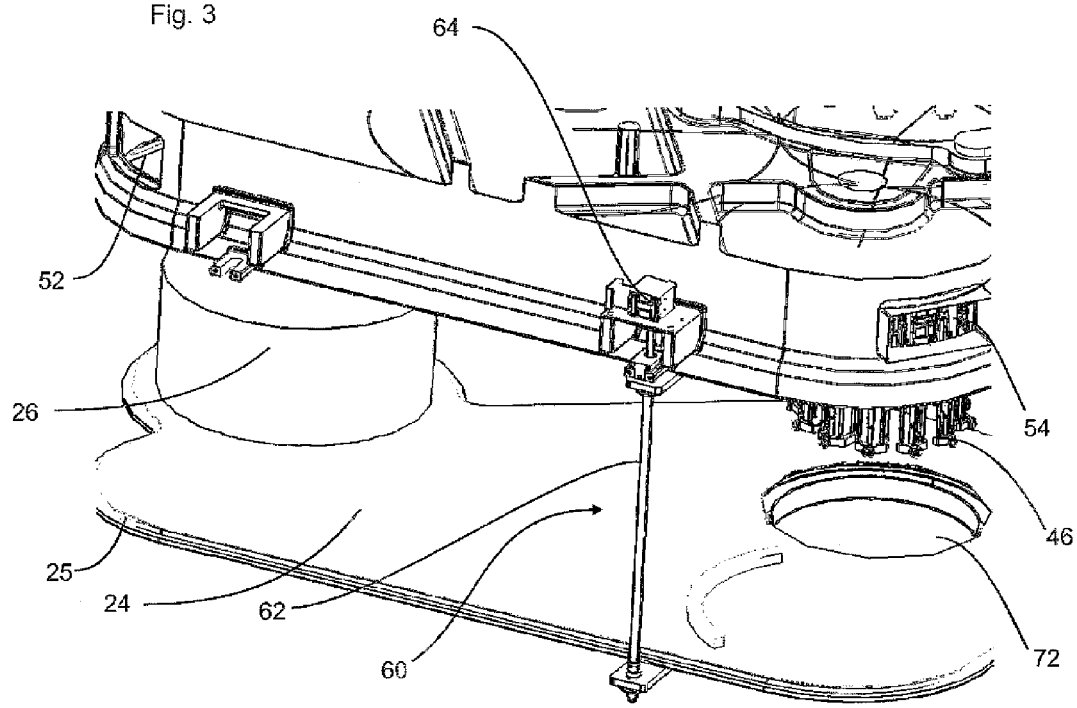

APPARATUS AND METHOD FOR STERILIZING CONTAINERS

CROSS-REFERENCE TO RELATED APPLICATIONS

A claim for priority under 35 U.S.C. §119 is made to German Patent Application No. 10 2013 109 794.4 filed Sep. 6, 2013 at the German Intellectual Property Office, the entire contents of which are hereby incorporated by reference.

FIELD

The present inventive concepts relate to an apparatus and a method for sterilizing containers, and in particular an apparatus and a method for sterilizing containers with a maintenance facility.

BACKGROUND

In the drink-producing industry, it is often usual to sterilize plastic containers, either preforms or finished bottles before they are filled. Conventional sterilization approaches included the use of substances such as hydrogen peroxide or peracetic acid. More recently, it has become more common to perform a sterilization of containers by an application of radiation, and in particular by bombardment with electrons or charge carriers. This bombardment with charge carriers is very efficient but generates undesirable radiation, and particular X-ray radiation. To assure the safety of plant parts and its operators, it is typical to screen the transport path along which the plastic containers are transported in order to prevent the escape of X-ray radiation.

SUMMARY

In accordance with an aspect of the present inventive concepts, provided is an apparatus for sterilizing containers, comprising: a transport device which transports the containers along a predefined transport path; and at least one sterilization device which bombards the containers with charge carriers for sterilization during a transport of the containers along the transport path. The at least one sterilization device comprises a generating device for generating charge carriers. The apparatus further comprises a screening device for screening radiation. The screening device surrounds the transport path of the containers at least in portions. The screening device comprises: a first wall adjacent the transport path of the containers; and a second wall below the transport path of the containers, wherein the second wall is movable relative to the transport path of the containers.

In some embodiments, the movement of the second wall forms an accessible opening to at least one sterilization device.

In some embodiments, the second wall is formed at least in portions as a support surface for an operator.

In some embodiments, the transport device has a movable carrier, and the apparatus further comprises a plurality of holding elements on the movable carrier that hold the containers.

In some embodiments, the second wall is movable in a longitudinal direction of the containers to be sterilized.

In some embodiments, the screening device at least in portions has a third wall which extends at the side adjacent the transport path of the containers, wherein the transport path at least in portions extends between the first wall and the third wall.

In some embodiments, the third wall is movable relative to the first wall.

In accordance with an aspect of the present inventive concepts, provided is a method for processing plastic containers, comprising: transporting the plastic containers along a predefined transport path in an operating mode; sterilizing, by a sterilization device, the plastic containers during the transporting of the plastic containers by bombarding the plastic containers with charge carriers; generating, by a charge carrier generating device, the charge carriers; and screening, by a screening device, X-ray radiation generated during sterilization of the plastic containers. The screening device has a first wall which extends at least in portions along the transport path of the plastic containers, and a second wall below the transport path of the plastic containers. The method further comprises moving in another operating mode the second wall to form an accessible opening to at least one region of the sterilization device.

In some embodiments, during sterilization, the plastic containers are transported through a transport channel which is formed by at least two side walls and the second wall, and the movement of the second wall exposes an opening located below the transport path, through which the region of the sterilization device is made accessible for the operator.

In some embodiments, both an outer wall and an inner wall of the plastic containers are bombarded with charge carriers.

In some embodiments, the second wall is movable in a longitudinal direction of the containers to be sterilized.

In some embodiments, the screening device at least in portions has a third wall which extends at the side adjacent the transport path of the containers, wherein the transport path at least in portions extends between the first wall and the third wall.

In some embodiments, the third wall is movable relative to the first wall.

BRIEF DESCRIPTION OF THE FIGURES

The above and other objects and features will become apparent from the following description with reference to the following figures, wherein like reference numerals refer to like parts throughout the various figures unless otherwise specified. In the drawings:

FIG. 3 shows a detailed depiction of the apparatus shown in FIG. 2.

DETAILED DESCRIPTION

Figure 1:
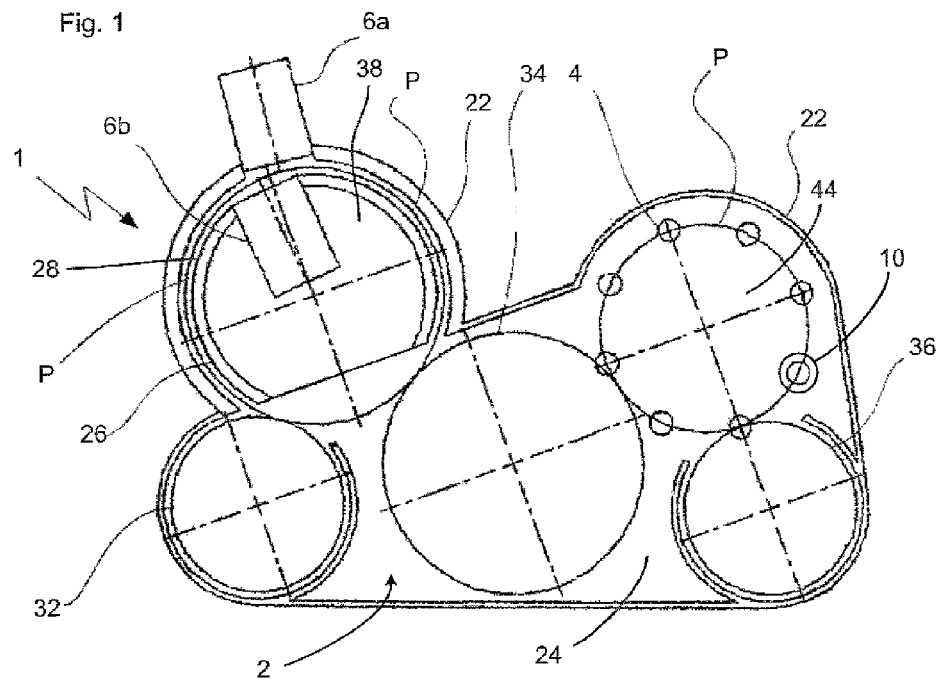
FIG. 1 is a view of an apparatus for sterilizing containers, in accordance with some embodiments.

Embodiments will be described in detail with reference to the accompanying drawings. The inventive concept, however, may be embodied in various different forms, and should not be construed as being limited only to the illustrated embodiments. Rather, these embodiments are provided as examples so that this disclosure will be thorough and complete, and will fully convey the concept of the inventive concept to those skilled in the art. Accordingly, known processes, elements, and techniques are not described with respect to some of the embodiments of the inventive concept. Unless otherwise noted, like reference numerals denote like elements throughout the attached drawings and written description, and thus descriptions will not be repeated. In the drawings, the sizes and relative sizes of layers and regions may be exaggerated for clarity.

It will be understood that, although the terms "first", "second", "third", etc., may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the inventive concept.

Spatially relative terms, such as "beneath", "below", "lower", "under", "above", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" or "under" other elements or features would then be oriented "above" the other elements or features. Thus, the exemplary terms "below" and "under" can encompass both an orientation of above and below. The device may be otherwise oriented (rotated 90 degrees or at other orientations) and the spatially relative descriptors used herein interpreted accordingly. In addition, it will also be understood that when a layer is referred to as being "between" two layers, it can be the only layer between the two layers, or one or more intervening layers may also be present.

The terminology used herein is for the purpose of describing particular embodiments only and is not intended to be limiting of the inventive concept. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Also, the term "exemplary" is intended to refer to an example or illustration.

It will be understood that when an element or layer is referred to as being "on", "connected to", "coupled to", or "adjacent to" another element or layer, it can be directly on, connected, coupled, or adjacent to the other element or layer, or intervening elements or layers may be present. In contrast, when an element is referred to as being "directly on," "directly connected to", "directly coupled to", or "immediately adjacent to" another element or layer, there are no intervening elements or layers present.

Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and/or the present specification and will not be interpreted in an idealized or overly formal sense unless expressly so defined herein.

There is often a safety-related need to design, construct and operate a sterilizer which is hermetically sealed and radiation-proof, and in particular to protect the region exposed to radiation.

The safety region in an apparatus, in particular in the packaging and foodstuffs sector, must fulfill two opposing requirements. First, the screening function must be ensured. Second, access to this region must be as favourable as possible, in particular for maintenance purposes. In conventional approaches, several service openings are provided which allowed access for operators. However, the greater the number of such service openings, the more extensive necessary safety and control measures are required for monitoring these connections. On the other hand, the fewer openings that are provided, the worse the access to the safety region.

Embodiments of the present inventive concepts are therefore based on an object of ensuring firstly a favourable screening effect and secondly a favourable accessibility for maintenance purposes. In other words, the inventive concepts are based on the object of improving as far as possible the accessibility and safety for such packaging sterilization devices using charge carriers, in particular, electrons.

In some embodiments, an apparatus for sterilizing containers has a transport device which transports the containers to be sterilized along a predefined transport path. Furthermore the apparatus has at least one sterilization device which exposes the containers to sterilization with charge carriers during their transport. The sterilization device has a generator device for generating charge carriers.

In addition, the apparatus has a screening device which serves to screen radiation, and in particular, radiation occurring during the sterilization process and/or during bombardment of the plastic containers with electron radiation. Furthermore, the screening device surrounds the transport path of the containers at least in portions. The screening device may extend at least in portions along the transport path and/or at the side next to the transport path of the containers. Extension along the transport path need not necessarily mean that for example the screening device is curved in the same manner as the transport path. For example, it may be sufficient if one wall, where applicable also with varying portions, extends along the transport path. For example, a wall may extend along a rectilinear portion to screen a curved transport path of the plastic preforms. Arrangement at the side means that this wall is provided at least in portions in a horizontal plane starting from the transport path.

Advantageously, the screening device at least in portions includes a wall. The wall can be made from a material which screens X-ray radiation, for example, lead having a sufficient thickness. The wall is constructed and arranged to screen the transport path of the plastic preforms in at least one direction standing perpendicular to the transport path. Advantageously, however, a course of the wall is adapted at least in portions to a course of the transport path. The wall can also be arranged so that it screens the X-ray radiation which is emitted directly by the individual sterilization devices. It is preferable for the screening device to surround the transport path of the containers substantially completely, except for any supply and discharge openings.

According to embodiments of the inventive concepts, the screening device comprises a first wall which is arranged at the side next to the transport path of the containers, and a second wall which is arranged below the transport path of the containers, and below the containers transported. At least the second wall is movable in relation to the (geometric) transport path of the containers. The second wall lies vertically below the transport path of the plastic containers. The transport path of the containers is preferably stationary.

The walls form an isolator within which the plastic containers are transported. The isolator can be configured so that this can be opened in full or at least in parts, and in particular opened downward, and preferably opened downward by a shift movement of a floor region. In this case, therefore, preferably, just one of six possible planes are separated from the others, in contrast to a preferably fixed remainder. In this way, accessibility can be improved for maintenance and similar purposes, and at the same time a favourable screening effect can be achieved when the isolator is in the closed state. The second wall is preferably a floor wall.

In some embodiments, the apparatus has an isolator within which the plastic containers are transported. This isolator can be opened for maintenance purposes or the like. In particular, the isolator can be opened in precisely one plane or in one direction. The screening device or radiation-screening device can have a part which is stationary during transport of the containers along the transport path. The radiation-screening device also has a part which is movable during transport of the containers along the transport path. In particular, the device can have a part which is movable relative to the stationary part.

In another embodiment, the apparatus has an interior bombardment device for sterilizing at least a portion of an inner wall of the containers. The apparatus also has an exterior bombardment device for sterilizing at least a portion of an outer wall of the containers. An apparatus for sterilizing the inner wall of the containers has, for at least part of the time, a lower acceleration voltage than the exterior bombardment device for sterilizing an outer wall of the plastic containers.

The apparatus performing an exterior sterilization of the plastic preforms is arranged stationary in relation to the movement of the plastic preforms. In another embodiment, the interior treatment device has at least one rod-like body which can be introduced into an interior of the containers through the mouth. Furthermore, the interior treatment device has an acceleration device for accelerating charge carriers, and an outlet window which is composed such that it can be introduced into the plastic containers through the mouth. Preferably, the charge carriers are charged particles, and in particular, electrons.

The apparatus has a plurality of such interior treatment devices, which are advantageously arranged on a moving carrier. In some embodiments, the moving carrier is a rotatable carrier.

The apparatus also has a plurality of holding elements for holding the plastic containers. In another embodiment, at least one interior bombardment device has an outlet window through which the charge carriers, and in particular, electrons, can emerge from a conduction chamber for conducting these charge carriers. Advantageously the outlet window is a film, and in particular a titanium film. In some embodiments, the film has a thickness between 6 µm and 20 µm. In some embodiments, the film has a thickness between 8 µm and 16 µm. In some embodiments, the film has a thickness between 8 µm and 12 µm.

In some embodiments, the second wall is formed of one piece. In other embodiments, the second wall is formed of several pieces, where in particular the two pieces can also be moved in relation to each other. In another embodiment, the screening device has a cover device which is preferably arranged above the transport path of the plastic containers and in particular above the plastic containers. In this manner, the screening can extend upward. The terms "bottom" and "top" here describe a vertical direction. This means that "bottom" is equivalent to nearer the ground, and "top" is equivalent to further away from the earth center. Preferably the cover device is arranged movably in the transport direction of the containers. Holding elements can also be arranged on this cover device for holding the plastic containers.

In another embodiment, the apparatus has rotation devices which rotate the plastic containers, at least in portions, during transport about a longitudinal direction of the plastic containers. This rotation preferably takes place at least in a portion of the transport path in which the plastic containers are sterilized on their outer surfaces. In this manner, the outer surface of the containers can be sterilized more evenly.

A movement of the second wall creates access to at least one sterilization device for operator intervention. Accordingly, due to said movement of the second wall, a service or maintenance opening can be formed. In particular, an opening is created which is sufficiently large for an operator to carry out maintenance work through this opening. The opening can be configured of such a size that some or all of an operator can enter the apparatus through the opening. Preferably, the movement of the second wall creates access to several sterilization devices.

The movement of the second wall permits access to all sterilization devices which serve for interior sterilization of the containers. Preferably, the movement of the second wall also creates access to all sterilization devices which serve for exterior sterilization of the containers. The movement of just one wall or two walls can provide access to the entire plant for operator intervention and/or maintenance work.

Advantageously, bombardment elements are provided within the screening device, so that plant parts such as gripper clamps, transport stars and the like can be sterilized.

In another embodiment, the wall is formed at least in portions as a support surface for an operator. This means that the wall is constructed for bearing the weight of an operator and for absorbing masses or weights of up to at least 150 kg. A drive device can be provided, by means of which the movement of the second wall can be achieved in relation to the transport path and in particular also in relation to the first wall.

As stated above, the transport device preferably has a movable carrier on which a plurality of holding elements is arranged for holding the containers. The holding elements can but not exclusively include gripper clamps which grip the containers in the predefined portion, for example, below the mouth or below the carrier ring. The second wall is movable, in particular, slidable, relative to the rotatable carrier. The movability means that the wall can be movable in relation to this carrier, even when the carrier is in a rest state, for example, where the carrier is rotatable but not rotating in the rest state.

In another embodiment, the second wall is movable, in particular in a longitudinal direction of the containers to be sterilized. This is preferably also a direction which stands perpendicular to the transport path of the plastic containers. In particular, the transport path is arranged to be circular or in a circle segment shape. The direction in which the wall is movable stands perpendicular to a plane formed by this orbit. The second wall can be movable in a direction vertical, i.e., in a direction which stands vertically to the longitudinal direction of the containers to be sterilized.

A movement device for moving the second wall can comprise one or more drives, for example, spindle drives, which allow lowering of the second wall in relation to the first wall for maintenance purposes.

In another embodiment, the screening device at least in portions has a third wall which runs at the side next to the transport path of the containers. The transport path at least in portions runs between the first wall and the third wall. In this embodiment, the first wall and the third wall preferably form a channel within which the plastic containers are transported. Preferably the plastic containers are sterilized on their outer surface during their transport through the channel.

At least one sterilization device can be integrated in the first and/or the third wall. In another embodiment, at least one sterilization device is integrated in the first wall and at least one sterilization device in the third wall. Preferably the two sterilization devices are arranged to be offset to each other along the transport path of the plastic preforms.

In another embodiment, the third wall is movable relative to the first wall. This is particularly advantageous for creating access to the channel between these walls by said movement of the third wall in relation to the first wall, and in particular also to the sterilization devices arranged at the walls.

The third wall can be arranged on the second wall, i.e., the floor wall, and/or a movement of the third wall is coupled to a movement of the second wall. If the second wall is lowered in this manner, at the same time the third wall is lowered in relation to the first wall, and hence at the same time the channel between the first wall and the third wall is opened.

The third wall can be directly coupled integrally with the floor. In this manner, the channel between the walls can be opened. Preferably, the third wall is movable in the longitudinal direction of the containers. The channel between the first wall and the third wall can extend along a circle line at least in portions. The third wall can be arranged inside the first wall in relation to the circle line.

Embodiments of the present inventive concepts are furthermore directed at a method for treating plastic containers, wherein the plastic containers are transported in one working mode along a predefined transport path and during this transport bombarded with charge carriers by at least one sterilization device for sterilization. The charge carriers are generated and accelerated by a charge carrier generating device. Upon sterilization of the plastic containers, any X-ray radiation produced is screened by a screening device. The screening device has a first wall which at least in portions extends along the transport path of the plastic containers, and/or which screens this X-ray radiation in one direction. The screening device has a second wall which is formed below the transport path of the plastic containers, and in a further operating mode the second wall is moved in order to create access for an operator to at least one region of the sterilization device, in particular, an inner region, in which the transport path of the plastic containers also runs.

An isolator is formed within which the plastic containers are transported. The isolator is delimited at least also by said second wall. The screening device has two walls which delimit the transport path of the plastic containers at the side. The second wall also delimits the plastic preforms or their transport path at the bottom.

In another embodiment, the plastic containers are transported for sterilization through a transport channel which is formed by at least two side walls and the second wall. The movement of the second wall exposes an opening below the transport path which creates access to an inner region of the sterilization device for the operator. The inner region is in particular a region in which X-ray radiation occurs, which must be screened against the outer region to be delimited from this inner region. In some embodiments, the second mode is a maintenance mode.

In another method, both an outer wall of the plastic containers and an inner wall of the plastic containers are bombarded with charge carriers or radiation. Advantageously the charge carriers are electrons. However, other charge carriers can be provided, for example alpha particles or protons. The charge carriers are particles which have an electric charge. The transport path along which the plastic containers are transported can be circular or circle segment shaped. The plastic containers can be plastic preforms which can be expanded in an expansion process into plastic containers, for example, plastic bottles.

FIG. 1 is a view of an apparatus 1 for sterilizing containers 10, in accordance with some embodiments.

The containers 10 can be plastic preforms and/or bottles formed from the preforms 10. The plastic preforms 10 are supplied to the apparatus 1 via a supply opening (not shown) and a supply device 32, for example, configured as a supply star. An external sterilization of the plastic containers 10 can take place. The containers 10 are guided on a circular transport path portion past two exterior sterilization devices 6a and 6b, which can bombard an outer surface of the plastic containers 10 with charge carriers and in particular electrons. A transport element 38 such as the transport star transports the plastic containers 10 during their exterior sterilization. The transport element 38 can have a rotatable carrier on which a plurality of holding devices is arranged for holding the plastic containers 10.

The plastic containers 10 are transported to an interior sterilization device by a transport element 34. The transport element 34 can be a transfer star which also allows a pitch delay between the individual plastic containers 10. In the region of the exterior sterilization, the transport path of the plastic containers 10 is delimited both towards the outside by a peripheral wall 22 of the apparatus and towards the inside by a wall 26.

Second sterilization devices 4 are arranged on a common rotatable carrier 44. The second sterilization devices 4 each have rod-like bodies which can be introduced into an interior of the plastic containers 10 in order to bombard them with charge carriers. At their lower end, these rod-like bodies have an outlet window through which the charge carriers can emerge from these rod-like bodies. A transport device 2 comprises a collection of the individual transport elements 34, for example, described above.

With respect to exterior sterilization and on interior sterilization, however, undesirable X-ray radiation occurs which should be screened as far as possible. To this end, the peripheral wall 22 of the apparatus surrounds the complete transport path P of the plastic preforms 10. The peripheral wall 22 can for example be made from lead. The radiation is screened at the top by a cover 28 and at the bottom by a floor wall 24. The peripheral wall 22 and the floor wall 24 can comprise a screening device for screening radiation. A discharge device 36 discharges the sterilized containers 10 from the apparatus 1. The discharge device 36 can also be formed as a transport star or the like.

Figure 2:
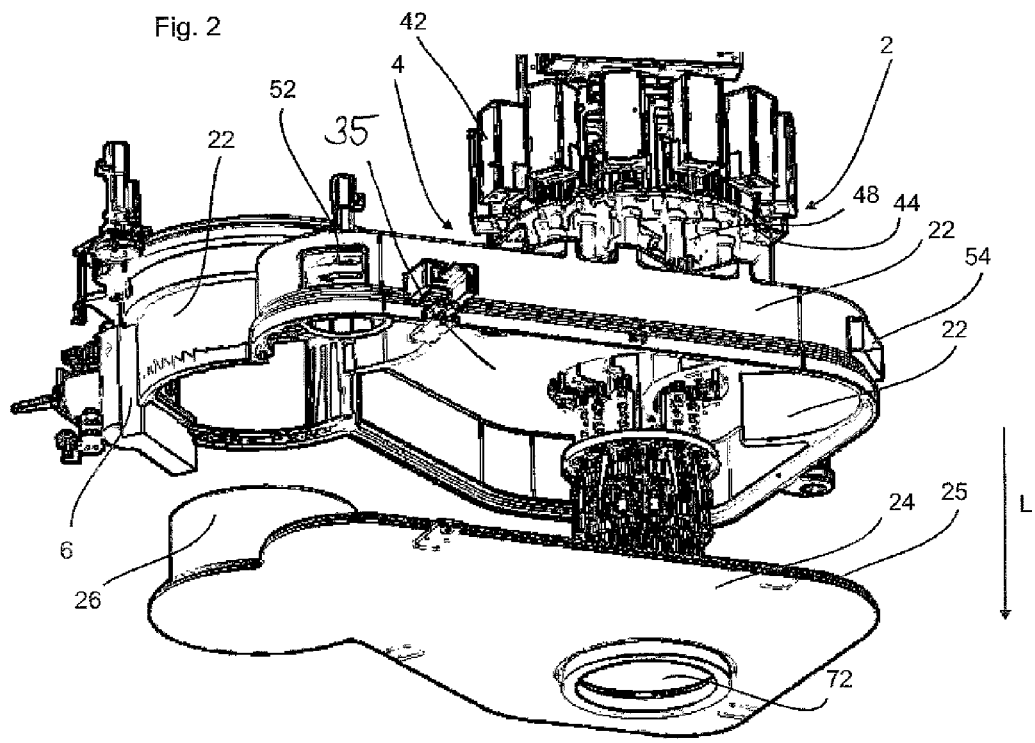
FIG. 2 shows a depiction of an apparatus in open state, in accordance with some embodiments.

FIG. 2 shows another depiction of an apparatus 1 for sterilizing plastic preforms 10. The apparatus 1 includes a first supply opening 52 via which the plastic preforms 10 are supplied to the apparatus 1, and a second opening via which the sterilized plastic preforms are discharged. Within the housing 20, in working mode a clean room can be formed so that sterilization of the plastic preforms also takes place under clean room conditions. Thus, both the first supply opening 52 and the discharge opening 54 have lock elements (not shown) which also serve to maintain a clean room.

As shown in FIG. 2, the floor wall 24 is lowered and thus the interior of the apparatus becomes accessible for maintenance work or other purpose for access. The wall portion 26 delimits the transport path P of the plastic preforms towards the inside, and is not formed together with the wall 22 but is instead arranged on the floor wall 24. In this way also the relatively narrow gap between the walls 22 and 26 in working mode can be opened by moving the two walls 22 and 26 apart. The floor wall 24 as stated above can also serve as a seating or standing surface for an operator, who can thus comfortably undertake maintenance work on the individual elements of the sterilization apparatus. The floor part or floor wall can be lowered in a direction L. This direction L is preferably parallel to the longitudinal direction of the plastic containers transported. In addition, between the floor wall 24 and the first wall, sealing means can be provided which safely prevent the emergence of disruptive radiation when the apparatus 1 is closed or in working mode. For example, on the floor part 24, a peripheral edge 25 extending in the direction of the side wall can be provided, which surrounds the side wall 22 at least partly and preferably completely when the apparatus is closed. Such an edge could also be arranged inside the side wall 22.

The individual sterilization devices 4 each have electron-generating devices 42 and acceleration devices which accelerate the electrons in the direction of the respective outlet window. Rod-like bodies 48 can be introduced into the interior of the plastic preforms. A further stationary cover wall 35 prevents the escape of (X-ray) radiation upward.

FIG. 3 shows an enlarged depiction of the apparatus shown in FIG. 2. Here, a drive device 60 is shown, which serves to raise and lower the floor part 28. The drive device 60 has a drive spindle and 62 and a drive element 64, such as an electric motor. As a whole, to lower and raise the floor part, several such drive devices are provided. An opening 62 is arranged in the floor part 24. Holding devices 46 hold plastic preforms to be sterilized. In a working mode, the plastic preforms can be raised and the radiation fingers thus introduced therein. The holding devices 48 can be introduced through the opening 72 when the floor part 24 is brought to the side wall 22. In a working mode, the containers can be raised into the sterilization chamber through the opening 72. This lift movement causes the radiation fingers to be inserted in the plastic containers. In a first operating mode, for example, production or sterilization, the floor is in the upper position and closes the clean room. In a second operating mode, for example, a maintenance mode, the floor is in the lowered state. After the conclusion of maintenance work, the entire clean room is resterilized before the first operating mode continues. Preferably this sterilization takes place after raising of the floor for floor maintenance.

The applicant reserves the right to claim all features disclosed in the application documents as essential to the invention where novel in relation to the prior art, individually or in combination.

What is claimed is:

1. An apparatus for sterilizing containers, comprising:
   transfer stars which transport the containers along a predefined transport path;
   at least one sterilization device which comprises an electron-generating device for generating charge carriers and which bombards the containers with charge carriers for sterilization of the containers during a transport of the containers along the transport path; and
   a screening device for screening radiation, the screening device surrounding the transport path of the containers at least in portions, wherein the screening device comprises:
   a first wall adjacent the transport path of the containers; and
   a second wall below the transport path of the containers, wherein the second wall includes a floor wall, and is movable relative to the transport path of the containers, and wherein a movement of the second wall exposes an accessible opening to the at least one sterilization device for operator intervention, wherein the opening is sufficiently large for an operator to carry out maintenance work through the opening.

2. The apparatus of claim 1, wherein the transport device has a movable carrier, and wherein the apparatus further comprises a plurality of holding elements on the movable carrier that hold the containers.

3. The apparatus of claim 1, wherein the second wall is movable in a longitudinal direction of the containers to be sterilized.

4. The apparatus of claim 1, wherein the screening device at least in portions has a third wall which extends at the side adjacent the transport path of the containers, wherein the transport path at least in portions extends between the first wall and the third wall.

5. The apparatus of claim 4, wherein the third wall is movable relative to the first wall.

6. The apparatus according to claim 1, wherein the screening device substantially completely surrounds the transport path of the containers.

7. The apparatus according to claim 1, wherein the walls form an isolator within which the containers are transported.

8. The apparatus according to claim 7, wherein the isolator is configured to be opened in full or at least in part.

9. The apparatus according to claim 8, wherein the isolator is opened downwards or is opened downwards by a shift movement of a floor region.

10. The apparatus according to claim 1, wherein the apparatus has an interior bombardment device for sterilizing at least a portion of an inner wall of the containers and an exterior bombardment device for sterilizing at least a portion of an outer wall of the containers.

11. An apparatus for sterilizing containers, comprising:
    transfer stars which transport the containers along a predefined transport path;
    at least one sterilization device which comprises an electron-generating device for generating charge carriers and which bombards the containers with charge carriers for sterilization of the containers during a transport of the containers along the transport path; and
    a screening device for screening radiation, the screening device surrounding the transport path of the containers at least in portions, wherein the screening device comprises:
    a first wall adjacent the transport path of the containers; and
    a second wall below the transport path of the containers, wherein the second wall is movable relative to the transport path of the containers, wherein the transfer stars have a movable carrier, and wherein the apparatus further comprises a plurality of holding elements on the movable carrier that hold the containers.

12. An apparatus for sterilizing containers, comprising:
transfer stars which transport the containers along a predefined transport path;
at least one sterilization device which comprises an electron-generating device for generating charge carriers and which bombards the containers with charge carriers for sterilization of the containers during a transport of the containers along the transport path; and
a screening device for screening radiation, the screening device surrounding the transport path of the containers at least in portions, wherein the screening device comprises:
 a first wall adjacent the transport path of the containers; and
 a second wall below the transport path of the containers, wherein the second wall is movable relative to the transport path of the containers, and wherein the screening device at least in portions has a third wall which extends at the side adjacent the transport path of the containers, wherein the transport path at least in portions extends between the first wall and the third wall, and wherein the third wall is movable relative to the first wall.

13. The apparatus according to claim 12, wherein the third wall and the first wall form a channel within which the containers are transported.

14. The apparatus according to claim 13, wherein the containers are sterilized on their outer surface during their transport through the channel.

15. The apparatus according to claim 12, wherein the third wall is arranged on the second wall and/or a movement of the third wall is coupled to a movement of the second wall.

16. The apparatus according to claim 12, wherein the second wall includes a floor wall.

17. The apparatus according to claim 12, wherein the containers are transported for sterilization through a transport channel, and wherein the transport channel is formed by at least two side walls and the second wall.

* * * * *